(12) United States Patent
Sakai et al.

(10) Patent No.: US 10,265,984 B2
(45) Date of Patent: Apr. 23, 2019

(54) CRYSTALLINE MODIFICATION OF N-(2-(3-PHENYLUREIDO)PHENYL) BENZENESULFONAMIDE AND RECORDING MATERIAL USING SAME

(71) Applicant: NIPPON SODA CO., LTD., Tokyo (JP)

(72) Inventors: Hiroshi Sakai, Ichihara (JP); Shuntaro Kinoshita, Ichihara (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 15/548,308

(22) PCT Filed: Feb. 17, 2016

(86) PCT No.: PCT/JP2016/000836
§ 371 (c)(1),
(2) Date: Aug. 2, 2017

(87) PCT Pub. No.: WO2016/136203
PCT Pub. Date: Sep. 1, 2016

(65) Prior Publication Data
US 2018/0022136 A1    Jan. 25, 2018

(30) Foreign Application Priority Data

Feb. 25, 2015   (JP) ................. 2015-035568
Mar. 27, 2015   (JP) ................. 2015-065613

(51) Int. Cl.
C07C 311/21   (2006.01)
B41M 5/333    (2006.01)
B41M 5/327    (2006.01)

(52) U.S. Cl.
CPC ......... *B41M 5/3333* (2013.01); *C07C 311/21* (2013.01); *B41M 5/3275* (2013.01); *C07B 2200/13* (2013.01)

(58) Field of Classification Search
CPC .... B41M 5/155; B41M 5/333; B41M 5/3333; B41M 5/3335; B41M 5/3336; B41M 2205/04; C07C 311/21; C07B 2200/13
USPC ........................................................ 503/216
See application file for complete search history.

(56) References Cited

U.S. PATENT DOCUMENTS

| 6,114,282 A | 9/2000 | Onishi et al. |
| 2015/0284321 A1 | 10/2015 | Sakai et al. |

FOREIGN PATENT DOCUMENTS

| CN | 1120094 C | 9/2003 |
| JP | H11-029549 A | 2/1999 |
| JP | 2004-189691 A | 7/2004 |
| JP | 2007-111972 A | 5/2007 |

(Continued)

OTHER PUBLICATIONS

Aug. 29, 2017 International Preliminary Report on Patentability issued in International Patent Application No. PCT/JP2016/000836.

(Continued)

*Primary Examiner* — Bruce H Hess
(74) *Attorney, Agent, or Firm* — Oliff PLC

(57) ABSTRACT

The disclosure provides a novel crystal form of N-(2-(3-phenylureido)phenyl)benzenesulfonamide, which is crystalline modification thereof specified by an X-ray diffraction diagram having peaks at diffraction angles (2θ±0.1°) of 23.60°, 20.80°, 12.24° and 13.80° in a powder X-ray diffractometry using Cu-Kα ray.

6 Claims, 2 Drawing Sheets

(56) References Cited

FOREIGN PATENT DOCUMENTS

| | | |
|---|---|---|
| JP | 2013-053117 A | 3/2013 |
| JP | 2015-013422 A | 1/2015 |
| WO | 2009/088549 A2 | 7/2009 |
| WO | 2014-080615 A1 | 5/2014 |

OTHER PUBLICATIONS

May 24, 2016 Search Report issued in International Patent Application No. PCT/JP2016/000836.

"4.3 Solution, Precipitation, Filtration, Dialysis 4.3.1 Solution a. Recrystallization, 4th Edition Experimental Chemistry Course 1 Basis Operation I" edited by The Chemical Society of Japan, issued by Maruzen Co., Ltd. (1990) pp. 184-186.

Hiroshi Oshima, "4.3.3 Crystallization, Chemical Handbook Applied Chemistry Edition," 6th Edition issued by Maruzen Co., Ltd. (Jan. 2003) pp. 178.

[Figure 1]
X-ray diffraction diagram of crystal form I
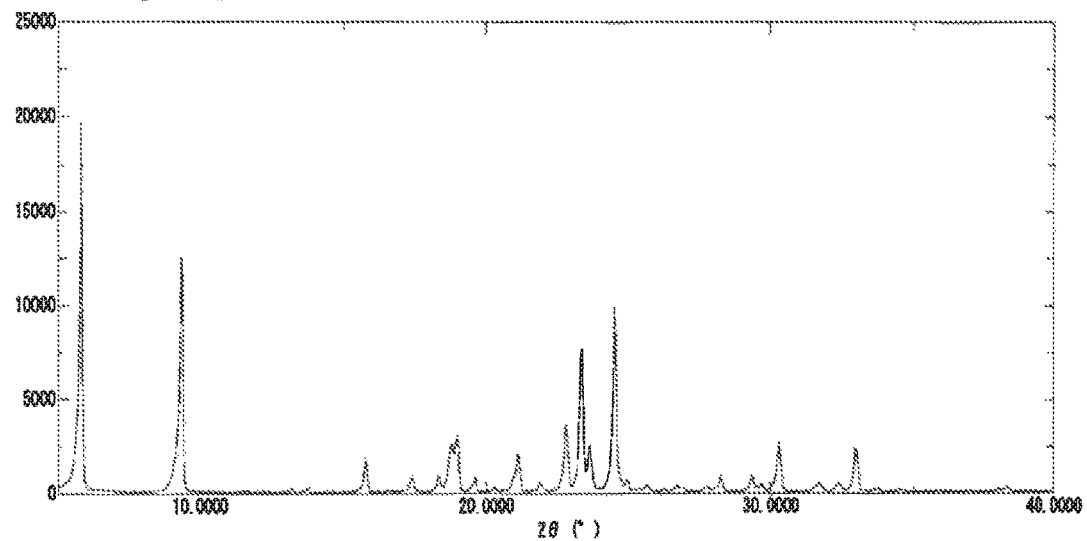

[Figure 2]
X-ray diffraction diagram of crystal form II
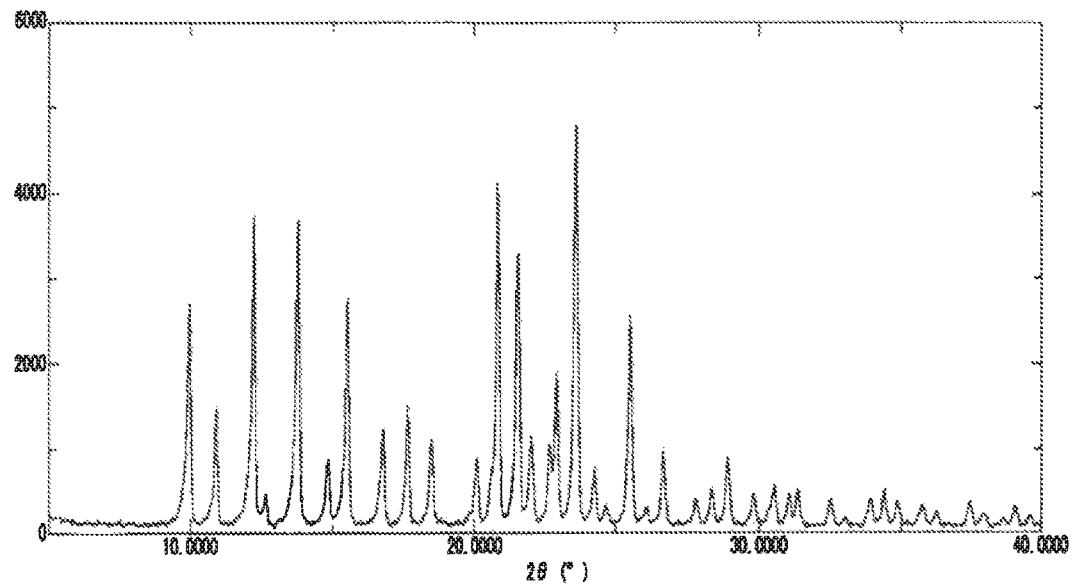

CRYSTALLINE MODIFICATION OF N-(2-(3-PHENYLUREIDO)PHENYL) BENZENESULFONAMIDE AND RECORDING MATERIAL USING SAME

TECHNICAL FIELD

The present invention relates to a novel crystal form of N-(2-(3-phenylureido)phenyl)benzenesulfonamide. The present application claims priority of Japanese Patent Application No. 2015-035568 filed on Feb. 25, 2015 and priority of Japanese Patent Application No. 2015-065613 filed on Mar. 27, 2015, the contents of which are incorporated herein by reference.

BACKGROUND ART

The recording material employing color development through a reaction between a color former and a color-developing agent, since record may be made by a relatively simple apparatus in a short time without applying a complicated treatment such as development and fixation, are widely used in e.g., thermal recording paper for output-recording from a facsimile, a printer or the like, or pressure-sensitive copying paper of a ledger sheet for simultaneous copying to several sheets.

Among the compounds serving as a color-developing agent, some compounds are known to have different crystal forms (see, Patent Documents 1, 2, 3). The present inventors have already proposed a recording material using a non-phenol compound such as N-(2-(3-phenylureido)phenyl)benzenesulfonamide as a color-developing agent and having excellent e.g., background heat-resistance (see Patent Document 4). Such non-phenol compounds are known not only as a color-developing agent but also a useful compound in medicinal use (see, Patent Document 5). Whether a compound having different crystal forms is present in these compounds has not yet been known. However, a compound may have different properties in using as a recording material depending upon the difference in crystal form. If such a crystal form is present, it will be extremely useful.

PRIOR ART DOCUMENTS

Patent Documents

Patent Document 1: Japanese unexamined Patent Application Publication No. H11-029549
Patent Document 2: Japanese unexamined Patent Application Publication No. 2004-189691
Patent Document 3: Japanese unexamined Patent Application Publication No. 2013-53117
Patent Document 4: International Publication WO 2014/080615
Patent Document 5: International Publication WO 2009/088549

SUMMARY OF INVENTION

Object to be Solved by the Invention

An object of the present invention is to provide a novel crystal form of N-(2-(3-phenylureido)phenyl)benzenesulfonamide.

Means to Solve the Object

The present inventors conducted studies on crystal form of N-(2-(3-phenylureido)phenyl)benzenesulfonamide in various conditions. As a result, they found N-(2-(3-phenylureido)phenyl)benzenesulfonamide having a novel crystal form. Based on the finding, the present invention has been completed.

More specifically, the present invention relates to (1) A crystalline modification of N-(2-(3-phenylureido)phenyl)benzenesulfonamide specified by an X-ray diffraction diagram having peaks at diffraction angles (2θ±0.1°) of 23.60°, 20.80°, 12.24° and 13.80° in powder X-ray diffractometry using Cu-Kα ray;

(2) The crystalline modification of N-(2-(3-phenylureido)phenyl)benzenesulfonamide according to (1) wherein a melting point is 160-162° C.;

(3) A recording material comprising a color former, wherein the recording material comprises the crystalline modification of N-(2-(3-phenylureido)phenyl)benzenesulfonamide according to (1) or (2); and (4) A recording sheet having a recording material layer formed from the recording material according to (3).

Effect of the Invention

According to the present invention, a novel crystal form of N-(2-(3-phenylureido)phenyl)benzenesulfonamide may be provided.

BRIEF DESCRIPTION OF DRAWINGS

FIG. 1 is an X-ray diffraction diagram of crystal form I showing peaks at 5.80°, 9.32°, 24.52° and 23.40°.

FIG. 2 is an X-ray diffraction diagram of crystal form II showing peaks at, 23.60°, 20.80°, 12.24° and 13.80°.

MODE OF CARRYING OUT THE INVENTION

N-(2-(3-phenylureido)phenyl)benzenesulfonamide (hereinafter sometimes referred to as Compound 1) is a compound represented by formula (1):

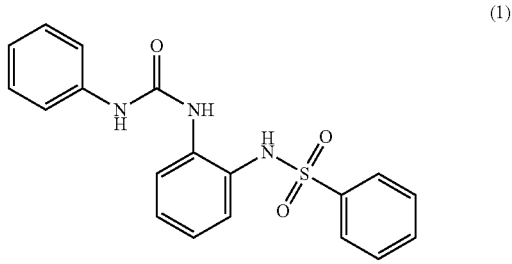 [SMILES: O=C(Nc1ccccc1)Nc1ccccc1NS(=O)(=O)c1ccccc1]

(1)

A crystal form (crystal form I) of Compound 1 known in the art is characterized by having peaks at diffraction angles (2θ; error of ±0.1° is acceptable) of 5.80°, 9.32°, 24.52° and 23.40° in powder X-ray diffractometry by Cu-Kα line and has a melting point of 153-155° C.

In contrast, the crystal form (crystal form II) of the present invention is characterized by having peaks at diffraction angles of 23.60°, 20.80°, 12.24° and 13.80° in powder X-ray diffractometry by Cu-Kα ray and has a melting point of 160-162° C.

(Crystalline Modification)

Crystalline modification refers to a state where crystal form differs while the composition is the same, with the result that physical properties change.

Whether the crystal forms are the same or different may be determined by measuring the incident angles of X-ray diffraction and the diffraction intensities thereof and comparing them. More specifically, comparison may be made by comparing the positions (angles) of diffraction lines at which high intensities are exhibited in powder X-ray diffraction diagrams.

There are cases where thermal properties such as a melting point differ depending on the crystal form. In such case, the crystal form may be determined simply by thermal analysis. If such a compound is used as e.g., a color-developing agent in a recording material, the thermal properties thereof may have an effect on the performance of the recording material.

As another determination method, e.g., IR (infrared spectroscopy) analysis is known.

(X-Ray Diffractometry)

A method of measuring X-ray diffraction is not particularly limited and a method generally employed may be used. Specifically, X-ray diffraction may be measured by grinding a crystal form in an agate mortar, charging the ground material in a glass sample plate, and subjecting the plate to measurement by in-plane multipurpose X-ray diffraction system (Ultima IV; manufactured by Rigaku Corporation).

(Measurement Method for Melting Point)

Melting point may be measured, for example, by hand or by use of a digital melting-point measuring device at a heating rate of 10° C./minute, by using each crystal form as a measurement sample.

(Manufacturing Method)

Compound 1 may be manufactured as a crystal form I by the method described in e.g., Patent Document 4. In contrast, crystal form II of the present invention may be obtained by recrystallization from crystal form I.

Crystal form I may be obtained by preparing a solution of crystal form II and recrystallizing therefrom by using crystal form I as a seed crystal.

(Use as Recording Material)

The crystalline modification of the present invention may be used as a color-developing agent in a recording material, together with a color former. The color-developing agent may be used in combination with another type of color-developing agent and further in combination with additives such as a sensitizer and an image stabilizer. The recording material may be applied to any use, for example, as e.g., a thermal recording material or a pressure-sensitive copying material.

N-(2-(3-phenylureido)phenyl)benzenesulfonamide (Compound 1) to be used as a color-developing agent is rarely decomposed with water, and has excellent color-developing performance, heat-resistance and resistance to plasticizer as a color-developing agent.

In addition, since this compound is a non-phenol compound, a safe recording material and recording sheet having no risk of endocrine disruption may be provided.

In the case where N-(2-(3-phenylureido)phenyl)benzenesulfonamide (Compound 1) is used as a color-developing agent, the crystalline modification (crystal form II) of the present invention may be used alone or in combination with the conventional crystal form I. Crystal form I and crystal form II may be used in any ratio. In such case, crystal form I and crystal form II, which are separately produced, may be mixed when a recording material is produced; alternatively, a mixture of crystal form I and crystal form II may be produced and used when Compound 1 is produced.

The ratio of Compound 1 to be used is usually 0.01 to 10 parts by mass, preferably 0.5 to 10 parts by mass, and further preferably 1.0 to 5 parts by mass with respect to 1 part by mass of the color former.

(Other Components in Recording Material)

In the recording material of the present invention, other than a color former and Compound 1, one or more chemical agents known in the art, such as a color-developing agent, an image stabilizer, a sensitizer, a filler, a dispersant, an antioxidant, a desensitizer, an anti-adhesive agent, an antifoaming agent, a light stabilizer and a fluorescent brightener, may be contained, if necessary. The amount of each of the other components falls usually in the range of 0.1 to 15 parts by mass and preferably 1 to 10 parts by mass with respect to 1 part by mass of the color former.

These chemical agents may be contained in a color developing layer. In case of a multi-layer structure, the chemical agents may be contained in any layer, for example, a protecting layer. Specifically, when the color developing layer particularly has an overcoat layer and/or an undercoat layer (on and/or under the color forming layer), e.g., an antioxidant and a light stabilizer may be contained in these layers. Furthermore, an antioxidant and a light stabilizer may be encapsulated, if necessary, in microcapsules, and then added to these layers.

As a color former to be used in the recording material of the present invention, a leuco dye such as a fluoran dye, a phthalide dye, a lactam dye, a triphenylmethane dye, a phenothiazine dye, a spiropyran dye or the like may be exemplified, however, the color former is not limited to these. Any color former may be used as long as it develops color by being in contact with a color-developing agent as an acidic substance. Although these color formers may be used alone to produce a recording material having color specified by the color former beyond any doubt, they may be used by combination of two or more thereof. For example, color formers of three primary colors, red, blue and green or a black color former may be used in combination to produce a recording material developing jet black.

As the fluoran color former, for example, 3,3-bis(p-dimethylaminophenyl)-phthalide, 3,3-bis(p-dimethylaminophenyl)-6-dimethylaminophthalide (also called as crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-cyclohexylamino-6-chlorofluoran, 3-dimethylamino-5,7-dimethylfluoran, 3-N-methyl-N-isopropylamino-6-methyl-7-anilinofluoran, 3-N-methyl-N-isobutylamino-6-methyl-7-anilinofluoran, 3-N-methyl-N-isoamylamino-6-methyl-7-anilinofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-(N-p-tolyl-N-ethylamino)-6-methyl-7-anilinofluoran, 3-pyrrolidino-6-methylamino-7-anilinofluoran, 2-{N-(3'-trifluoromethylphenyl)amino}-6-diethylaminofluoran, 2-{3,6-bis(diethylamino)-9-(o-chloroanilino)xanthylbenzoic acid lactam}, 3-diethylamino-6-methyl-7-(m-trichloromethylanilino)fluoran, 3-diethylamino-7-(o-chloroanilino)fluoran, 3-dibutylamino-7-(o-chloroanilino) fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-diethylamino-6-methyl-7-(2',4'-dimethylanilino)fluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6- methyl-7-anilinofluoran, 3-(N-ethyl-N-propylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-pyrrolidino-6-methyl-7-anilinofluoran, 3-piperidino-6-methyl-7-anilinofluoran, 3-dimethylamino-7-(m-trifluoromethylanilino) fluoran, 3-dipentylamino-6-methyl-7-anilinofluoran, 3-(N-ethoxypropyl-N-ethyl-amino)-6-methyl-7-anilinofluoran, 3-dibutylamino-7-(o-fluoroanilino) fluoran, 3-diethylaminobenzo[a]fluoran, 3-diethylamino-5-methyl-7-benzylaminofluoran, 3-diethyl-amino-5-chlorofluoran, 3-diethylamino-6-(N,N'-dibenzy-lamino)fluoran, 3,6-dimethoxyfluoran, 2,4-dimethyl-6-(4-dimethylaminophenyl)aminofluoran, 3-diethylamino-7-(m-trifluoromethylanilino) fluoran, 3-diethylamino-6-methyl-7-octylaminofluoran, 3-diethylamino-6-methyl-7-(m-tolylamino)fluoran, 3-diethylamino-6-methyl-7-(2,4-xylylamino)fluoran, 3-diethylamino-7-(o-fluoroanilino) fluoran, 3-diphenylamino-6-methyl-7-anilinofluoran;

benzoylleucomethylene blue, 6'-chloro-8'-methoxy-ben-zoindolino-spiropyran, 6'-bromo-3'-methoxy-benzoin-dolino-spiropyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl) phthalide, 3-(2'-hydroxy-4'-diethylaminophenyl)-3-(2'-methoxy-5'-methylphenyl)phthalide, 3-(2'-methoxy-4'-dimethylaminophenyl)-3-(2'-hydroxy-4'-chloro-5'-methylphenyl)phthalide, 3-morpholino-7-(N-propyl-trifluoromethylanilino)fluoran, 3-pyrrolidino-7-trifluoromethylanilinofluoran, 3-diethylamino-5-chloro-7-(N-benzyl-trifluoromethylanilino) fluoran, 3-pyrrolidino-7-(di-p-chlorophenyl)methylaminofluoran, 3-diethylamino-5-chloro-7-(α-phenylethylamino)fluoran, 3-(N-ethyl-p-toluidino)-7-(α-phenylethylamino)fluoran, 3-diethylamino-7-(o-methoxycarbonylphenylamino) fluoran, 3-diethylamino-5-methyl-7-(α-phenylethylamino) fluoran, 3-diethylamino-7-piperidinofluoran, 2-chloro-3-(N-methyl-toluidino)-7-(p-n-butylanilino)fluoran, 3-(N-methyl-N-iso-propylamino)-6-methyl-7-anilinofluoran, 3-dibutylamino-6-methyl-7-anilinofluoran, 3-dipentylamino-6-methyl-7-anilinofluoran, 3,6-bis(dimethylamino)fluorenespiro(9,3')-6'-dimethylaminophthalide, 3-(N-benzyl-N-cyclohexylamino)-5,6-benzo-7-α-naphthylamino-4'-bromofluoran, 3-diethylamino-6-chloro-7-anilinofluoran, 3-N-ethyl-N-(2-ethoxypropyl)amino-6-methyl-7-anilino-fluoran, 3-N-ethyl-N-tetrahydrofurfurylamino-6-methyl-7-anilinofluoran, 3-diethylamino-6-methyl-7-mesitydino-4',5'-benzofluoran, or 3-(N-ethyl-p-toluidino)-7-(methylphenylamino)fluoran may be exemplified.

Among these color formers, 3,3-bis(p-dimethylamino-phenyl)-6-dimethylaminophthalide, 3-cyclohexylamino-6-chlorofluoran, 3-diethylamino-7-chlorofluoran, 3-diethyl-amino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-diethylamino-7-(o-chloroanilino) fluoran, 3-dibutylamino-7-(o-chloroanilino) fluoran, 3-N-methyl-N-cyclohexylamino-6-methyl-7-anilinofluoran, 3-(N,N-diethylamino)-5-methyl-7-(N,N-dibenzylamino) fluoran, 3-(N,N-diethylamino)-7-(N,N-dibenzylamino)fluo-ran, 3-(N-ethyl-N-isobutylamino)-6-methyl-7-anilinofluo-ran, 3-(N-methyl-N-propylamino)-6-methyl-7-anilinofluo-ran, 3-(N-ethyl-N-isopentylamino)-6-methyl-7-anilinofluoran, 3-(N-ethyl-N-toluidino)-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylamino-7-(m-trifluoromethylanilino) fluoran, 3-diethylamino-6-methyl-7-octylaminofluoran, 3-diethylamino-6-methyl-7-(m-tolylamino)fluoran, 3-diethylamino-7-(o-fluoroanilino)fluoran, 3-diphenylamino-6-methyl-7-anilinofluoran, benzoyl leuco methylene blue, 3-dibutylamino-6-methyl-7-anilinofluoran, 3-N-ethyl-N-tetrahydrofurfurylamino-6-methyl-7-anilino-fluoran, 3-(N-ethyl-p-toluidino)-7-(methylphenylamino) fluoran or the like may be preferably exemplified.

As a near infrared absorbing dye, 3-[4-[4-(4-anilino)-anilino]anilino]-6-methyl-7-chlorofluoran, 3,3-bis[2-(4-di-methylaminophenyl)-2-(4-methoxyphenyl)vinyl]-4,5,6,7-tetrachlorophthalide, 3,6,6'-tris(dimethylamino)spiro (fluorene-9,3'-phthalide) or the like may be exemplified.

Compound 1 is suitably used as a color-developing agent mainly in thermal recording materials and may be used alone or in combination with a plurality of color-developing agents known in the art in any ratio.

As specific examples of the other color-developing agents, the following ones may be exemplified.

Bisphenol compounds such as bisphenol A, 4,4'-sec-butyl-idenebisphenol, 4,4'-cyclohexylidenebisphenol, 2,2'-bis(4-hydroxyphenyl)-3,3'-dimethylbutane, 2,2'-dihydroxydiphe-nyl, pentamethylene-bis(4-hydroxybenzoate), 2,2-dimethyl-3,3-di(4-hydroxyphenyl)pentane, 2,2-di(4-hydroxyphenyl) hexane, 2,2-bis(4-hydroxyphenyl) propane, 2,2-bis(4-hy-droxyphenyl)butane, 2,2-bis(4-hydroxy-3-methylphenyl) propane, 4,4'-(1-phenylethylidene)bisphenol, 4,4'-ethyliden-ebisphenol, (hydroxyphenyl)methylphenol, 2,2'-bis(4-hydroxy-3-phenyl-phenyl)propane, 4,4'-(1,3-phenylenediisopropylidene)bisphenol, 4,4'-(1,4-phenylenediisopropylidene)bisphenol, and butyl 2,2-bis(4-hydroxyphenyl)acetate; sulfur-containing bisphenol compounds such as 4,4'-dihydroxydiphenyl thioether, 1,7-di(4-hydroxyphenylthio)-3,5-dioxaheptane, 2,2'-bis(4-hy-droxyphenylthio)diethyl ether, and 4,4'-dihydroxy-3,3'-dim-ethyldiphenyl thioether; 4-hydroxybenzoic acid esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxy-benzoate, and diphenylmethyl 4-hydroxybenzoate; metal salts of benzoic acid such as zinc benzoate and zinc 4-ni-trobenzoate; salicylic acids such as 4-[2-(4-methoxypheny-loxy)ethyloxy]salicylic acid; metal salts of salicylic acid such as zinc salicylate and zinc bis[4-(octyloxycarbo-nylamino)-2-hydroxybenzoate];

hydroxysulfones such as 4,4'-dihydroxydiphenylsulfone, 2,4'-dihydroxydiphenylsulfone, 4-hydroxy-4'-methyldiphe-nylsulfone, 4-hydroxy-4'-isopropoxydiphenylsulfone, 4-hy-droxy-4'-butoxydiphenylsulfone, 4,4'-dihydroxy-3,3'-dially-ldiphenylsulfone, 3,4-dihydroxy-4'-methyldiphenylsulfone, 4,4'-dihydroxy-3,3',5,5'-tetrabromodiphenylsulfone, 4-ally-loxy-4'-hydroxydiphenylsulfone, 2-(4-hydroxyphenylsulfo-nyl) phenol, 4,4'-sulfonylbis[2-(2-propenyl)]phenol, 4-[{4-(propoxy)phenyl}sulfonyl]phenol, 4-[{4-(allyloxy) phenyl}sulfonyl]phenol, 4-[({4-(benzyloxy) phenyl}sulfonyl]phenol, and 2,4-bis(phenylsulfonyl)-5-methyl-phenol; polyvalent metal salts of hydroxysulfones such as a zinc, magnesium, aluminum or titanium salt of 4-phenylsulfonylphenoxy; 4-hydroxyphthalic acid diesters such as dimethyl 4-hydroxyphthalate, dicyclohexyl 4-hy-droxyphthalate and diphenyl 4-hydroxyphthalate;

hydroxynaphthoic acid esters such as 2-hydroxy-6-car-boxynaphthalene; trihalomethylsulfones such as tribromom-ethylphenylsulfone; sulfonylureas such as 4,4'-bis(p-tolu-enesulfonylaminocarbonylamino)diphenylmethane, and N-(4-methylphenylsulfonyl)-N'-(3-(4-methylphenylsulfonyloxy)phenyl)urea; hydroxyacetophenone, p-phenylphenol, benzyl 4-hydroxyphenylacetate, p-benzylphenol, hydroquinone-monobenzyl ether, 2,4-dihydroxy-2'-methoxybenzanilide, tetracyanoquinodimethanes, N-(2-hydroxyphenyl)-2-[(4-hydroxyphenyl) thio]acetamide, N-(4-hydroxyphenyl)-2-[(4-hydroxyphenyl) thio]acetamide, 4-hydroxybenzenesulfonanilide, 4'-hydroxy-4-methylbenzenesulfonanilide, 4,4'-bis((4-methyl-3-phenoxycarbonyl)aminophenylureido)diphenylsulfone, 3-(3-phenylureido)benzenesulfonanilide, octadecylphosphoric acid, or dodecylphosphoric acid; and cross-linked diphenylsulfone compounds (color-developing agent D-90 manufactured by Nippon Soda Co., Ltd.) represented by the following Formula or mixtures thereof, or the like may be exemplified.

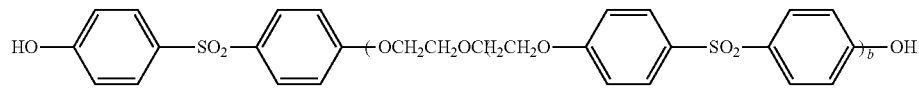

(b is an integer of 0 to 6)

Among them, 4-hydroxy-4'-isopropoxydiphenylsulfone, cross-linked diphenylsulfone compounds or mixtures thereof may be preferably mentioned.

As the image stabilizer, for example, epoxy group-containing diphenylsulfones such as 4-benzyloxy-4'-(2-methylglycidyloxy)-diphenylsulfone, and 4,4'-diglycidyloxydiphenylsulfone; 1,4-diglycidyloxybenzene, 4-[α-(hydroxymethyl)benzyloxy]-4'-hydroxydiphenylsulfone, 2-propanol derivatives, salicylic acid derivatives, metal salts of oxynaphthoic acid derivatives (particularly zinc salts), metal salts of 2,2-methylenebis(4,6-t-butylphenyl) phosphate, water-insoluble zinc compounds other than the above zinc compounds, hindered phenol compounds such as 2,2-bis(4'-hydroxy-3',5'-dibromophenyl)propane, 4,4'-sulfonyl-bis(2,6-dibromophenol), 4,4'-butylidene (6-t-butyl-3-methylphenol), 2,2'-methylene-bis(4-methyl-6-t-butylphenol), 2,2'-methylene-bis(4-ethyl-6-t-butylphenol), 2,2'-di-t-butyl-5,5'-dimethyl-4,4'-sulfonyldiphenol, 1,1,3-tris(2-methyl-4-hydroxy-5-cyclohexylphenyl)butane and 1,1,3-tris(2-methyl-4-hydroxy-5-t-butylphenyl)butane; and phenol novolak compounds, epoxy resins, or UU (urea-urethane compound manufactured by CHEMIPRO KASEI) may be exemplified.

In addition, cross-linked diphenylsulfone compounds (color-developing agent, D-90, manufactured by Nippon Soda Co., Ltd.) represented by the following formula or mixtures thereof may be exemplified.

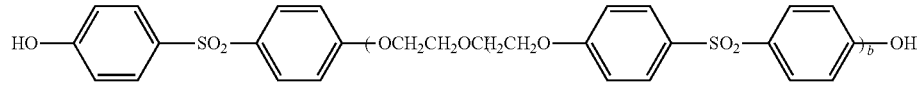

(b is an integer of 0 to 6)

Among them, UU and D-90 are preferable.
It is noted that, the image stabilizer is preferably a compound being solid at normal temperature and particularly preferably a compound having a melting point of 60° C. or more and being less soluble in water.

As the sensitizer, for example,
higher fatty acid amides such as stearic acid amide, stearic acid anilide, and palmitic acid amide; amides such as benzamide, acetoacetanilide, thioacetoanilide acrylic acid amide, ethylenebisamide, ortho-toluenesulfonamide and para-toluenesulfonamide; phthalic acid diesters such as dimethyl phthalate, dibenzyl isophthalate, dimethyl isophthalate, dimethyl terephthalate, diethyl isophthalate, diphenyl isophthalate and dibenzyl terephthalate; oxalic acid diesters such as dibenzyl oxalate, di(4-methylbenzyl) oxalate, di(4-chlorobenzyl) oxalate, a mixture of dibenzyl oxalate and di(4-chlorobenzyl) oxalate in equal amounts, and a mixture of di(4-chlorobenzyl) oxalate and di(4-methylbenzyl) oxalate in equal amounts; bis(t-butylphenols) such as 2,2'-methylenebis(4-methyl-6-t-butylphenol) and 4,4'-methylene-bis-2,6-di-t-butylphenol; 4,4'-dihydroxydiphenylsulfone diethers such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexyloxydiphenylsulfone, and 4,4'-diallyloxydiphenylsulfone; 2,4'-dihydroxydiphenylsulfone diethers such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone, 2,4'-dihexyloxydiphenylsulfone, and 2,4'-diallyloxydiphenylsulfone;
1,2-bis(phenoxy)ethane, 1,2-bis(4-methylphenoxy)ethane, 1,2-bis(3-methylphenoxy)ethane, 1,2-bis(phenoxymethyl)benzene, 1,2-bis(4-methoxyphenylthio) ethane, 1,2-bis(4-methoxyphenoxy) propane, 1,3-phenoxy-2-propanol, 1,4-diphenylthio-2-butene, 1,4-diphenylthiobutane, 1,4-diphenoxy-2-butene, 1,5-bis(4-methoxyphenoxy)-3-oxapentane, 1, 3-dibenzoyloxypropane, dibenzoyloxymethane, 4,4'-ethylenedioxy-bis-benzoic acid dibenzyl ester, bis[2-(4-methoxy-phenoxy)ethyl] ether, 2-naphthylbenzyl ether, 1,3-bis(2-vinyloxyethoxy)benzene, 1,4-diethoxynaphthalene, 1,4-dibenzyloxynaphthalene, 1,4-dimethoxynaphthalene, 1,4-bis(2-vinyloxyethoxy)benzene, p-(2-vinyloxyethoxy)biphenyl, p-aryloxybiphenyl, p-propargyloxybiphenyl, p-benzyloxybenzyl alcohol, 4-(m-methylphenoxymethyl)biphenyl, 4-methylphenyl-biphenyl ether, di-β-naphthylphenylenediamine, diphenylamine, carbazole, 2,3-di-m-tolylbutane, 4-benzylbiphenyl and 4,4'-dimethylbiphenyl;
terphenyls such as m-terphenyl and p-terphenyl;
1,2-bis(3,4-dimethylphenyl)ethane, 2,3,5,6-tetramethyl-4'-methyldiphenylmethane, 4-acetylbiphenyl, dibenzoylmethane, triphenylmethane, phenyl 1-hydroxy-naphthoate, methyl 1-hydroxy-2-naphthoate, N-octadecylcarbamoyl-p-methoxycarbonylbenzene, benzyl p-benzyloxybenzoate, phenyl β-naphthoate, methyl p-nitrobenzoate or diphenylsulfone;

carbonic acid derivatives such as diphenyl carbonate, guaiacol carbonate, di-p-tolyl carbonate and phenyl-α-naphthyl carbonate;

1,1-diphenylpropanol, 1,1-diphenylethanol, N-octadecylcarbamoylbenzene, dibenzyl disulfide, stearic acid, amide AP-1 (a mixture of stearic acid amide and palmitic acid amide in a ratio of 7:3);

stearates such as aluminum stearate, calcium stearate and zinc stearate; and zinc palmitate, behenic acid, zinc behenate, montanic acid wax and polyethylene wax may be exemplified.

Preferably, 2-naphthylbenzyl ether, m-terphenyl, 4-benzylbiphenyl, benzyl oxalate, di(4-chlorobenzyl) oxalate, a mixture of dibenzyl oxalate and di(4-chlorobenzyl) oxalate in equal amounts, di(4-methylbenzyl) oxalate, a mixture of di(4-chlorobenzyl) oxalate and di(4-methylbenzyl) oxalate in equal amounts, phenyl 1-hydroxy-2-naphthoate, 1,2-bis(phenoxy)ethane, 1,2-bis(3-methylphenoxy)ethane, 1,2-bis(phenoxymethyl)benzene, dimethyl terephthalate, stearic acid amide, amide AP-1 (a mixture of stearic acid amide and palmitic acid amide in a ratio of 7:3), diphenylsulfone, or 4-acetylbiphenyl may be mentioned.

Further preferably, di(4-methylbenzyl) oxalate, 1,2-bis(3-methylphenoxy) ethane, 1,2-bis(phenoxymethyl)benzene, diphenylsulfone, 2-naphthylbenzyl ether or the like may be mentioned.

As the filler, for example, silica, clay, kaolin, calcined kaolin, talc, satin white, aluminum hydroxide, calcium carbonate, magnesium carbonate, zinc oxide, titanium oxide, barium sulfate, magnesium silicate, aluminum silicate, plastic pigment, diatomaceous earth, talc or aluminum hydroxide may be exemplified. Among them, calcined kaolin or calcium carbonate may be suitably exemplified. The ratio of the filler to be used is 0.1 to 15 parts by mass and preferably 1 to 10 parts by mass with respect to 1 part by mass of the color former. Alternatively, the above fillers may be used as a mixture.

As the dispersant, for example, polyvinyl alcohol; a polyvinyl alcohol such as acetoacetylated polyvinyl alcohol, carboxy modified polyvinyl alcohol, sulfonic acid modified polyvinyl alcohol, amide modified polyvinyl alcohol, butyral modified vinyl alcohol, which differs in saponification degree and polymerization degree; a cellulose derivatives such as methylcellulose, carboxymethylcellulose, hydroxyethylcellulose, ethylcellulose, acetylcellulose and hydroxymethylcellulose; sodium polyacrylate, polyacrylic acid ester, polyacrylamide, starch; sulfosuccinate esters such as dioctyl sodium sulfosuccinate; sodium dodecylbenzene sulfonate, sodium salt of lauryl alcohol sulfuric acid ester, fatty acid salt, styrene-maleic anhydride copolymers, styrene-butadiene copolymers, polyvinyl chloride, polyvinyl acetate, polyacrylic acid ester, polyvinylbutyral, polyurethane, polystyrene and copolymers thereof, polyamide resins, silicone resins, petroleum resins, terpene resins, ketone resins and a coumarone resin may be exemplified.

The dispersant is dissolved in a solvent such as water, an alcohol, a ketone, an ester and a hydrocarbon and then put in use or may be emulsified or dispersed like a paste in water or another solvent and then put in use.

As the antioxidant, for example, 2,2'-methylenebis(4-methyl-6-t-butylphenol), 2,2'-methylenebis(4-ethyl-6-t-butylphenol), 4,4'-propyl methylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, 4-{4-[1,1-bis(4-hydroxyphenyl)ethyl]-α,α-dimethylbenzyl}phenol, 1,1,3-tris(2-methyl-4-hydroxy-5-cyclohexylphenyl)butane, 2,2'-methylenebis(6-t-butyl-4-methylphenol), 2,2'-methylenebis(6-t-butyl-4-ethylphenol), 4,4'-thiobis(6-t-butyl-3-methylphenol), 1,3,5-tris [{4-(1,1-dimethylethyl)-3-hydroxy-2,6-dimethylphenyl}methyl]-1,3,5-triazine-2,4,6(1H, 3H, 5H)-trione, and 1,3,5-tris[{3,5-bis(1,1-dimethylethyl)-4-hydroxyphenyl}methyl]-1,3,5-triazine-2,4,6 (1H, 3H, 5H)-trione may be exemplified.

As the desensitizer, for example, an aliphatic higher alcohol, polyethylene glycol, and a guanidine derivative may be exemplified.

As the anti-adhesive agent, for example, stearic acid, zinc stearate, calcium stearate, carnauba wax, paraffin wax and ester wax may be exemplified.

As the antifoaming agent, for example, a higher alcohol based antifoaming agent, a fatty acid ester based antifoaming agent, an oil based antifoaming agent, a silicone based antifoaming agent, a polyether based antifoaming agent, a modified hydrocarbon based antifoaming agent and a paraffin based antifoaming agent may be exemplified.

As the light stabilizer, for example, a UV absorber based on a salicylic acid such as phenyl salicylate, p-t-butylphenyl salicylate, and p-octylphenyl salicylate; a UV absorber based on benzophenone such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl) methane; an UV absorber based on benzotriazole such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-(2'-hydroxy-5'-t-butylphenyl)benzotriazole, 2-(2'-hydroxy-5'-(1",1",3",3"-tetramethylbutyl)phenyl)benzotriazole, 2'-[(2'-hydroxy-3'-(3"',4"',5"',6"'-tetrahydrophthalimidomethyl)-5'-methylphenyl]benzotriazole, 2-(2'-hydroxy-5'-t-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, 2,2'-methylenebis[4-(1,1,3,3-tetramethylbutyl)-6-(2H-benzotriazol-2-yl)]phenol, and a condensation product between polyethylene glycol and methyl-3-[3-t-butyl-5-(2H-benzotriazol-2-yl)-4-hydroxyphenyl] propionate; a UV absorber based on cyanoacrylate such as 2'-ethylhexyl-2-cyano-3,3-diphenylacrylate and ethyl-2-cyano-3,3-diphenylacrylate; a UV absorber based on hindered amine such as bis(2,2,6,6-tetramethyl-4-piperidyl) sebacate, bis(2,2,6,6-tetramethyl-4-piperidyl) succinate and bis(1,2,2,6,6-pentamethyl-4-piperidyl) 2-(3,5-di-t-butyl)malonate; and 1,8-dihydroxy-2-acetyl-3-methyl-6-methoxynaphthalene may be exemplified.

As the fluorescent brightener, for example, 4,4'-bis[2-anilino-4-(2-hydroxyethyl)amino-1,3,5-triazinyl-6-amino]stilbene-2,2'-disulfonic acid disodium salt, 4,4'-bis[2-anilino-4-bis(hydroxyethyl)amino-1,3,5-triazinyl-6-amino]stilbene-2,2'-disulfonic acid disodium salt, 4,4'-bis[2-anilino-4-bis(hydroxypropyl)amino-1,3,5-triazinyl-6-amino]stilbene-2,2'-disulfonic acid disodium salt, 4,4'-bis[2-methoxy-4-(2-hydroxyethyl)amino-1,3,5-triazinyl-6-amino]stilbene-2,2'-disulfonic acid disodium salt, 4,4'-bis[2-methoxy-4-(2-hydroxypropyl)amino-1,3,5-triazinyl-6-amino]stilbene-2,2'-disulfonic acid disodium salt, 4,4'-bis[2-m-sulfoanilino-4-bis(hydroxyethyl)amino-1,3,5-triazinyl-6-amino]stilbene-2,2'-disulfonic acid disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid hexasodium salt 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid hexasodium salt, 4,4'-bis[2-(2,5-disulfoanilino)-4-formalinylamino-1,3,5-triazinyl-6-amino]stilbene-2,2'-disulfonic acid hexasodium salt, and 4,4'-bis[2-(2,5-disulfoanilino)-4-bis(hydroxyethyl)amino-1,3,5-triazinyl-6-amino]stilbene-2,2'-disulfonic acid hexasodium salt may be exemplified.

(Method for Producing a Recording Material)

In the case where the present invention is used in thermal recording paper, the same manner as known in the art may be employed. For example, a thermal recording paper may be produced by dispersing fine particles of a compound of the present invention and fine particles of a color former separately in an aqueous solution of a water-soluble binder such as polyvinyl alcohol and cellulose to prepare suspension solutions, mixing the suspension solutions, applying the mixture onto a support made of e.g., paper, and drying the support.

In the case where the present invention is used in pressure-sensitive copying paper, the pressure-sensitive copying paper may be produced in the same manner as known in the case where a color-developing agent or a sensitizer is used. For example, a color former encapsulated in microcapsules by a method known in the art is dispersed with the help of an appropriate dispersant and the dispersion solution is applied onto paper to prepare a color former sheet. Furthermore, a dispersion solution of a color-developing agent is applied to paper to prepare a color-developing agent sheet. Both sheets thus prepared are combined to prepare a pressure-sensitive copying paper. As a pressure-sensitive copying paper, a unit consisting of an upper sheet having microcapsules containing an organic solvent solution of the color former applied onto the lower surface and a lower sheet having the color-developing agent (acidic substance) applied onto the upper surface, or a so-called self-content paper having the microcapsules and the color-developing agent applied onto the same sheet-surface may be used.

As the color-developing agent to be used herein or to be used by blending, a color-developing agent known in the art is used. For example, an inorganic acidic substance such as Japanese acid clay, activated clay, attapulgite, bentonite, colloidal silica, aluminum silicate, magnesium silicate, zinc silicate, tin silicate, calcined kaolin and talc; an aliphatic carboxylic acid such as oxalic acid, maleic acid, tartaric acid, citric acid, succinic acid and stearic acid; an aromatic acid such as benzoic acid, p-t-butyl benzoic acid, phthalic acid, gallic acid, salicylic acid, 3-isopropyl salicylic acid, 3-phenyl salicylic acid, 3-cyclohexyl salicylic acid, 3,5-di-t-butyl salicylic acid, 3-methyl-5-benzyl salicylic acid, 3-phenyl-5-(2,2-dimethylbenzyl) salicylic acid, 3,5-di-(2-methylbenzyl) salicylic acid, and 2-hydroxy-1-benzyl-3-naphthoic acid; metal salts (such as zinc, magnesium, aluminum and titanium) of these aromatic carboxylic acids; a phenol resin color-developing agent such as a p-phenyl phenol-formalin resin and p-butylphenol-acetylene resin; and a mixture of these phenol resin color-developing agents and a metal salt of the above aromatic carboxylic acid may be exemplified.

As the support to be used in the present invention, paper, synthetic paper, film, plastic film, foamed plastic film, nonwoven fabric, or recycled paper such as waste-paper pulp, conventionally known in the art or the like may be used. These may be used in combination as a support.

In the case where paper is used as a support, a dispersion solution containing a dye dispersion solution, a color-developing agent dispersion solution and a filler dispersion solution may be directly applied to the paper; however, a dispersion solution for an undercoat layer is applied in advance and dried, and then, the aforementioned dispersion solution may be applied. Preferably, the dispersion solution for an undercoat layer is applied, and then, the aforementioned dispersion solution is applied. This is because good color-developing sensitivity is obtained.

The dispersion solution for an undercoat layer is used in order to improve the surface smoothness of a support and particularly not limited; however, a filler, a dispersant and water are preferably contained. Specifically, as the filler, e.g., calcined kaolin or calcium carbonate is preferable. As the dispersant, e.g., polyvinyl alcohol is preferable.

In the case where a recording material layer is formed on a support, a method of applying a dispersion solution containing a dye dispersion solution, a color-developing agent dispersion solution and a filler dispersion solution to the support and drying the support is preferable. Other than this, a method of applying the dispersion solution by e.g., spraying followed by drying and a method of soaking a support in a dispersion solution for a predetermined time, followed by drying or the like may be exemplified. For applying the dispersion solution, a hand coating method, a size press coater method, a roll coater method, an air knife coater method, a blend coater method, a blow coater method, a curtain coater method, a comma direct method, a gravure direct method, a gravure reverse method, a reverse roll coater method or the like may be exemplified.

EXAMPLES

Now, the recording material of the present invention will be more specifically described by way of Examples; however, the present invention is not limited merely to these.

Production Example 1
(Production of Crystal Form I)

10.8 g (0.1 mol) of o-phenylenediamine (manufactured by Tokyo Kasei Kogyo Co., Ltd., purity: 98%) and 5.8 g (0.055 mol) of sodium carbonate were added to a mixed solvent of 10 ml of ethyl acetate and 70 ml of water. After nitrogen replacement, the solution was cooled to an inner temperature of 20° C. To the solution, 17.7 g (0.1 mol) of benzenesulfonyl chloride was added dropwise such that the inner temperature did not exceed 20° C. After the temperature was elevated up to 50° C., the reaction was carried out for 2 hours at the same temperature. After completion of the reaction, 90 ml of ethyl acetate was added and the temperature was elevated up to 60° C. The precipitated crystal was dissolved. After standing at the same temperature, the water layer was removed by phase separation.

After 50 ml of the solvent was evaporated from the organic layer, the organic layer was cooled to 50° C. and 11.9 g of phenyl isocyanate was added dropwise. A reaction was carried out at the same temperature for one hour. After completion of the reaction, 50 ml of an aliphatic hydrocarbon solvent was added and the mixture was cooled to 5° C. Crystals were separated by suction filtration and subjected to vacuum drying to obtain a desired product as white crystals (35.0 g, yield 95% with respect to o-phenylenediamine).

Example 1 (Production of Crystal Form II)

In a 100-ml four-neck flask, 11 g of the crystal obtained in Production Example 1 and 15 ml (0.5 L/mol) of ethyl acetate were added. The mixture was stirred at an inner temperature of 50° C. or more for 4 hours to completely dissolve. Thereafter, the inner temperature was decreased to 10° C. or less. The crystal generated was separated by filtration and dried under reduced pressure to obtain 10.2 g of white crystals (recovery rate: 91.6%).

(Measurement Example 1) Measurement of Diffraction Angle by Powder X-Ray Analysis Powder of the crystal obtained in Production Example 1 and the powder of the crystal obtained in Example 1 were each placed in sample filling sections in glass test plates and subjected to measurement by a powder X-ray diffractometer (Ultima IV; manufactured by Rigaku Corporation). X-ray source: CuKα, Power: 1.6 kW (40 kV-40 mA), Measurement range: 2θ=5° to 40°

The measurement result of the crystal (crystal form I) of Production Example 1 is shown in FIG. 1, and the measurement result of the crystal (crystal form II) of Example 1 is shown in FIG. 2.

Each crystal form showed the following strong peaks:
Crystal form I: 5.80°, 9.32°, 24.52°, 23.40°
Crystal form II: 23.60°, 20.80°, 12.24°, 13.80°

(Measurement Example 2) Measurement of Melting Point

Each crystal was used as a measurement sample and measurement was manually carried out.
The melting point of each crystal form was as follows:
Crystal form I: 153-155° C.
Crystal form II: 160-162° C.
From the results, it was found that crystal form II, which is the crystalline modification of the present invention, has different properties from crystal form I known in the art.

Example 2 (Method for Producing Crystal Form I from Crystal Form II)

In a 300-ml four-neck flask, 9.2 g of a crystal having crystal form I as mentioned above and 25 ml (1 L/mol) of ethyl acetate were added and dispersed at an inner temperature of 10° C. Then, 9.2 g of a crystal having crystal form II was added to 100 ml (4 L/mol) of ethyl acetate in a dripping funnel and completely dissolved by heating the mixture up to 70° C. While keeping the inner temperature of the dispersion solution of the crystal form I at 15° C. or less, and warming the dripping funnel by a ribbon heater such that the crystals of crystal form II did not precipitate, the solution of crystal form II was added dropwise to the dispersion solution of crystal form I. After completion of the dropwise addition, the inner temperature was decreased to 10° C. or less. The generated crystals generated were separated by filtration and dried under reduced pressure to obtain 12.4 g of crystals (recovery rate: 76.2%).

The powder X ray of the crystal obtained by the aforementioned method was measured. As a result, the same results as in crystal form I described in Measurement Example 1 were obtained. It was confirmed that the crystal is crystal form I.

Preparation and Test of Thermal Recording Paper
1) Preparation of Thermal Recording Paper
Undercoat-layer dispersion solution
Calcined kaolin
(Ansilex (registered trade mark)-93) 27.8 parts
Aqueous solution of 10% polyvinyl alcohol 26.2 parts
Water 71 parts
Dye dispersion solution (Solution A)
3-Di-n-butylamino-6-methyl-7-anilinofluoran 16 parts
Aqueous solution of 10% polyvinyl alcohol 84 parts
Color-developing agent dispersion solution (Solution B)
Crystal form (I or II) of Compound 1 16 parts
Aqueous solution of 10% polyvinyl alcohol 84 parts
Filler dispersion solution (Solution C)
Calcium carbonate 27.8 parts
Aqueous solution of 10% polyvinyl alcohol 26.2 parts
Water 71 parts
Additive dispersion solution (Solution D)
D-90 or UU 16 parts
Aqueous solution of 10% polyvinyl alcohol 84 parts
("parts" represents "parts by mass")

Example 3, Comparative Example 1 (Containing No Additive)

First, the undercoat layer-dispersion solution was applied to white paper in an amount of about 8 g/m$^2$ on a dry-mass basis, and the paper was dried to prepare an undercoat layer.

Then, each mixture having the composition of the Solutions A to D was sufficiently ground with a sand grinder to prepare dispersion solutions of the components of the Solutions A to D. Among them, 1 part by mass of the Solution A, 2 parts by mass of the Solution B, and 4 parts by mass of the Solution C were mixed to prepare a coating solution. The coating solution was applied to the paper having the undercoat layer by use of a wire rod (wire bar NO. 12, manufactured by Webster), and the paper was dried and then calendering treatment was applied to prepare a thermal recording paper (coating solution: about 5.5 g/m$^2$ on a dry-mass basis).

Examples 4, 5 and Comparative Examples 2, 3 (Containing Additives)

Thermal recording papers were prepared in the same manner as in Example 3 and Comparative Example 1 except that 1 part by mass of the Solution A, 2 parts by mass of the Solution B, 4 parts by mass of the Solution C and 1 part by mass of the Solution D were mixed to prepare a coating solution.

2) Saturated Color Development Test

On the thermal recording papers prepared in the aforementioned method, a checker board pattern was formed at a saturation color development by a thermos-sensitive paper color development test machine (TH-PMD type, manufactured by OHKURA-DENKI) in the conditions of a printing voltage of 17 V and a pulse width of 1.8 ms. After color development, the optical density was measured by a spectrophotometer (Spectroeye LT, manufactured by X-rite). The results are shown in Table 1.

TABLE 1

|  | Crystal form | Saturation density |
|---|---|---|
| Comparative Example 1 | I | 1.22 |
| Example 3 | II | 1.24 |

3) Storage Stability Test for Background

With respect to each thermal recording paper prepared by the aforementioned method, the test sheets before and after the test were subjected to a storage stability test in the following conditions.

[Before Test]

The thermal recording papers prepared by the aforementioned method were partly cut out and the optical density of the background was measured by a spectrophotometer (Spectroeye LT, manufactured by X-rite).

[Heat Resistance Test]

The thermal recording papers prepared in the above method were partly cut out and stored in an incubator (trade name: DK-400, manufactured by YAMATO) of 80° C. or 90° C. for 24 hours. After storage, the optical density of the background was measured by a spectrophotometer (Spectroeye LT, manufactured by X-rite). The results are shown in Table 2.

TABLE 2

|  |  |  |  | Background heat resistance | |
|---|---|---|---|---|---|
|  | Crystal form | Additive | Before test | 80° C., 24 h | 90° C., 24 h |
| Comparative Example 1 | I | — | 0.05 | 0.05 | 0.08 |
| Example 3 | II | — | 0.04 | 0.05 | 0.06 |
| Comparative Example 2 | I | D-90 | 0.05 | 0.07 | 0.20 |
| Example 4 | II | D-90 | 0.05 | 0.06 | 0.15 |
| Comparative Example 3 | I | UU | 0.05 | 0.06 | 0.07 |
| Example 5 | II | UU | 0.04 | 0.05 | 0.06 |

4) Image Storage Stability Test

With respect to thermal recording papers prepared by the aforementioned method, the test sheets were subjected to a storage stability test in the following conditions.

[Before Test]

The thermal recording papers prepared in the above method were partly cut out and color was developed by use of a thermo-sensitive paper color development test machine (trade name: TH-PMH type, manufactured by OHKURA-DENKI) at a printing voltage of 17 V and a pulse width of 1.8 ms. The density of colored image was measured by a spectrophotometer (Spectroeye LT, manufactured by X-rite).

[Heat Resistance Test]

The thermal recording papers prepared in the above method were partly cut out and saturated color development was carried out in the same manner as before the test. Then, each of the test sheets was stored in an incubator (trade name: DK-400, manufactured by YAMATO) of 80° C. or 90° C. for 24 hours. After the storage, the optical density thereof was measured by a spectrophotometer (Spectroeye LT, manufactured by X-rite). The results are shown in Table 3

TABLE 3

|  |  |  |  | Image heat resistance | |
|---|---|---|---|---|---|
|  | Crystal form | Additive | Before test | 80° C., 24 h | 90° C., 24 h |
| Comparative Example 1 | I | — | 1.34 | 1.36 | 1.29 |
| Example 3 | II | — | 1.34 | 1.34 | 1.23 |
| Comparative Example 2 | I | D-90 | 1.34 | 1.33 | 1.39 |
| Example 4 | II | D-90 | 1.36 | 1.35 | 1.39 |
| Comparative Example 3 | I | UU | 1.31 | 1.30 | 1.31 |
| Example 5 | II | UU | 1.33 | 1.33 | 1.31 |

[Test for Resistance to Plasticizer]

The thermal recording papers prepared in the above method were partly cut out and saturated color development was carried out in the same manner as before the test. Then, polyvinyl chloride wrap film (containing a plasticizer) was brought into contact with the color developing surface and the rear surface of each test paper and stored at 40° C. for 24 hours while keeping this state. After the test, the optical density thereof was measured by a spectrophotometer (Spectroeye LT, manufactured by X-rite).

[Water Resistance Test]

The thermal recording papers prepared in the above method were partly cut out and saturated color development was carried out in the same manner as before the test. Then the test paper was soaked in water at 25° C. for 24 hours. After the test, the optical density thereof was measured by a spectrophotometer (Spectroeye LT, manufactured by X-rite).

[Alcohol Resistance Test]

The thermal recording papers prepared in the above method were partly cut out and saturated color development was carried out in the same manner as before the test. Then the test paper was soaked in a 35% ethanol solution at 25° C. for one hour. After the test, the optical density thereof was measured by a spectrophotometer (Spectroeye LT, manufactured by X-rite).

The resistance to plasticizer, water resistance and alcohol resistance are collectively shown in Table 4.

TABLE 4

|  | Crystal form | Additive | Before test | Resistance to plasticizer 40° C., 24 h | Water resistance 25° C., 24 h | Alcohol resistance 25° C., 1 h |
|---|---|---|---|---|---|---|
| Comparative Example 1 | I | — | 1.34 | 0.18 | 1.08 | 0.93 |
| Example 3 | II | — | 1.34 | 0.10 | 1.12 | 0.92 |

TABLE 4-continued

| | Crystal form | Additive | Before test | Resistance to plasticizer 40° C., 24 h | Water resistance 25° C., 24 h | Alcohol resistance 25° C., 1 h |
|---|---|---|---|---|---|---|
| Comparative Example 2 | I | D-90 | 1.34 | 1.21 | 1.15 | 1.07 |
| Example 4 | II | D-90 | 1.36 | 1.16 | 1.15 | 1.00 |
| Comparative Example 3 | I | UU | 1.31 | 1.14 | 1.15 | 1.14 |
| Example 5 | II | UU | 1.33 | 1.09 | 1.17 | 1.18 |

In the case where crystal form II was used as Compound 1, the performance equal to or more excellent than that of crystal form I was obtained. With respect to background heat-resistant, crystal form II tends to be more excellent. In particular, when D-90 was used in combination, fogging occurred at 90° C. in the background in the case of crystal form I; however, in the case of crystal form II, fogging slightly occurred but fell within an acceptable range. With the respect to the resistance to plasticizer in the above conditions, the resistance was relatively poor in the case where no additive was used; however, when D-90 or UU was used in combination as an additive, a sufficient resistance was shown for all crystal forms.

The invention claimed is:

1. A crystalline modification of N-(2-(3-phenylureido) phenyl)benzenesulfonamide specified by an X-ray diffraction diagram having peaks at diffraction angles (2θ±0.1°) of 23.60°, 20.80°, 12.24° and 13.80° in a powder X-ray diffractometry using Cu-Kα ray.

2. The crystalline modification of N-(2-(3-phenylureido) phenyl)benzenesulfonamide according to claim 1, wherein a melting point is 160-162° C.

3. A recording material comprising a color former, wherein the recording material comprises the crystalline modification of N-(2-(3-phenylureido)phenyl)benzenesulfonamide according to claim 2.

4. A recording sheet having a recording material layer formed from the recording material according to claim 3.

5. A recording material comprising a color former, wherein the recording material comprises the crystalline modification of N-(2-(3-phenylureido)phenyl)benzenesulfonamide according to claim 1.

6. A recording sheet having a recording material layer formed from the recording material according to claim 5.

* * * * *